United States Patent [19] [11] 4,015,066
Nagata et al. [45] Mar. 29, 1977

[54] CRYSTALLINE MONOSODIUM N⁶,2'-O-DIBUTYRYL-ADENOSINE-3',5'-CYCLIC MONOPHOSPHATE AND PRODUCTION THEREOF

[75] Inventors: Takashi Nagata; Goro Motoki; Morio Suzuki; Hiroshi Yoshino, all of Choshi, Japan

[73] Assignee: Yamasa Shoyu Kabushiki Kaisha, Japan

[22] Filed: Apr. 8, 1974

[21] Appl. No.: 459,203

[30] Foreign Application Priority Data

Apr. 6, 1973 Japan .............................. 48-38756
Apr. 6, 1973 Japan .............................. 48-38757

[52] U.S. Cl. .................................. 536/27; 424/180
[51] Int. Cl.² .......................................... C07H 19/20
[58] Field of Search ................ 260/211.5 R; 536/27

[56] References Cited

UNITED STATES PATENTS 3,849,397  11/1974  Robins et al. ................ 260/211.5 R
3,852,267  12/1974  Meyer, Jr. et al. ......... 260/211.5 R
3,856,776  12/1974  Cehovic et al. ............. 260/211.5 R Primary Examiner—Johnnie R. Brown
Attorney, Agent, or Firm—Wenderoth, Lind & Ponack

[57] ABSTRACT

Crystalline N⁶,2'-O-dibutyryl-adenosine-3',5'-cyclic monophosphate monosodium salt ($DB_c$-AMP-$N_a$), and a process for producing the same which may comprise the step of causing at least one solvent selected from an ether, ketone, and an ester, constituting a crystallizing organic solvent, to contact an alcoholic solution, aqueous alcoholic solution, or a simple aqueous solution of $DB_c$-AMP-$N_a$ or may comprise the step of dissolving crude crystalline or amorphous $DB_c$-AMP-$N_a$ in a mixture of an alcoholic solvent and the crystallizing organic solvent.

9 Claims, 3 Drawing Figures

CRYSTALLINE MONOSODIUM N⁶,2'-O-DIBUTYRYL-ADENOSINE-3',5'-CYCLIC MONOPHOSPHATE AND PRODUCTION THEREOF

BACKGROUND OF THE INVENTION

This invention relates to $N^6,2'$-O-dibutyryl-adenosine-3',5'-cyclic monophosphate monosodium sald (hereinafter abbreviated to $DB_c$-AMP-$N_a$) in a crystalline form, and in another aspect thereof to a process for producing $DB_c$-AMP-$N_a$ in a crystalline form. According to the latter aspect of this invention, the process for producing $DB_c$-AMP-$N_a$ in a crystalline form is characterized in that at least one kind of compound selected from an ether, a ketone, and an ester, as a crystallizing organic solvent, is caused to contact an alcoholic solution, aqueous alcoholic solution, or a simple aqueous solution of $DB_c$-AMP-$N_a$ thereby to precipitate the $DB_c$-AMP-$N_a$ out of the solution in a crystal form.

Alternatively, the process may comprise the steps of dissolving $DB_c$-AMP-$N_a$ in a crude crystalline state or in an amorphous state in a mixture of the above-mentioned alcoholic liquid and the crystallizing organic solvent thereby to recrystallize the $DB_c$-AMP-$N_a$.

Adenosine-3',5'-cyclic monophosphate is naturally distributed widely in various biological worlds and has an important role in the vital phenomena thereof. $DB_c$-AMP-$N_a$, which is a useful derivative of the adenosine-3',5'-cyclic monophosphate, is recently attracting wide attention, and various fields of application therefor such as for medicine and biochemical reagents are now rapidly developed.

Heretofore, $DB_c$-AMP-$N_a$ has been prepared as non-crystalline powder by freeze-drying, vacuum-drying, or some other method, out of its solution. However, since $DB_c$-AMP-$N_a$ itself is extremely unstable, the purification thereof to a satisfactory degree is not practicable, and impurities (such as salts, coloring matters, or other minor ingredients) have been always contained in the resulting powdery product. Furthermore, the resultant $DB_c$-AMP-$N_a$ in the form of non-crystalline powder is also unstable. This and the above described feature together with its extremely high hygroscopic property frequently constitute serious limitations in the production and the application of the product.

SUMMARY OF THE INVENTION

As a result of various studies we have carried out in depth on processes for crystallization of high purification effectivenes and with promise of solution of the problems such as stability and hygroscopicity, we have discovered that crystals of high purity and high stability can be obtained by causing at least one kind of crystallizing organic solvent from among on ether, a ketone, an ester, and the like to contact an alcoholic solution, an aqueous alcoholic solution, or an aqueous solution of $DB_c$-AMP-$N_a$. We have found further that this crystalline $DB_c$-AMP-$N_a$, in comparison with noncrystalline products known heretofore, has extremely high purity and high stability and does not have hygroscopicity.

The invention will be better understood from the following detailed description of the invention with respect to preferred embodiments thereof when read in conjunction with the accompanying illustrations and practiced examples.

BRIEF DESCRIPTION OF THE ILLUSTRATIONS

In the illustrations:

The particulars of X-ray diffraction analysis are as follows:

| | |
|---|---|
| X-Ray Target | Cu (Ni) |
| X-Ray Intensity | 35 KVP.15ma |
| Detector | GM.1200V° |
| Scanning Speed | 1°/min. |
| Slit First | 1° |
| Second | 0.2 mm |
| Third | 1° |
| Chart Speed | 10 mm./min. |
| Time Constant | 2 sec. |
| Multiplier | 0.8 |
| Operation | 1 |
| Scale Factor | 8 |
| Chart Full Scale | 1000. o.p.s. |

DETAILED DESCRIPTION

Crystallography

Figure 1:
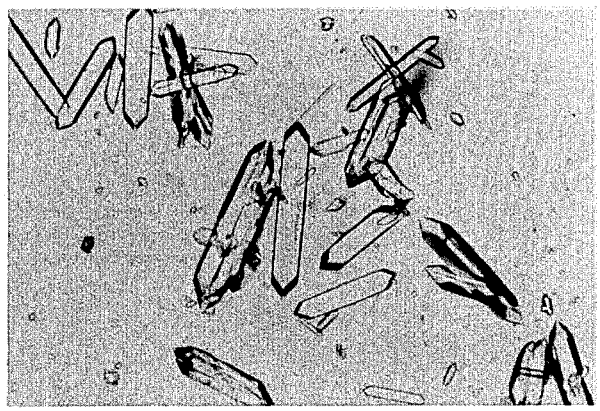
FIG. 1 is a photomicrograph showing crystalline $DB_c$-AMP-$N_a$ crystallized from its solution in dioxane.
Figure 2:
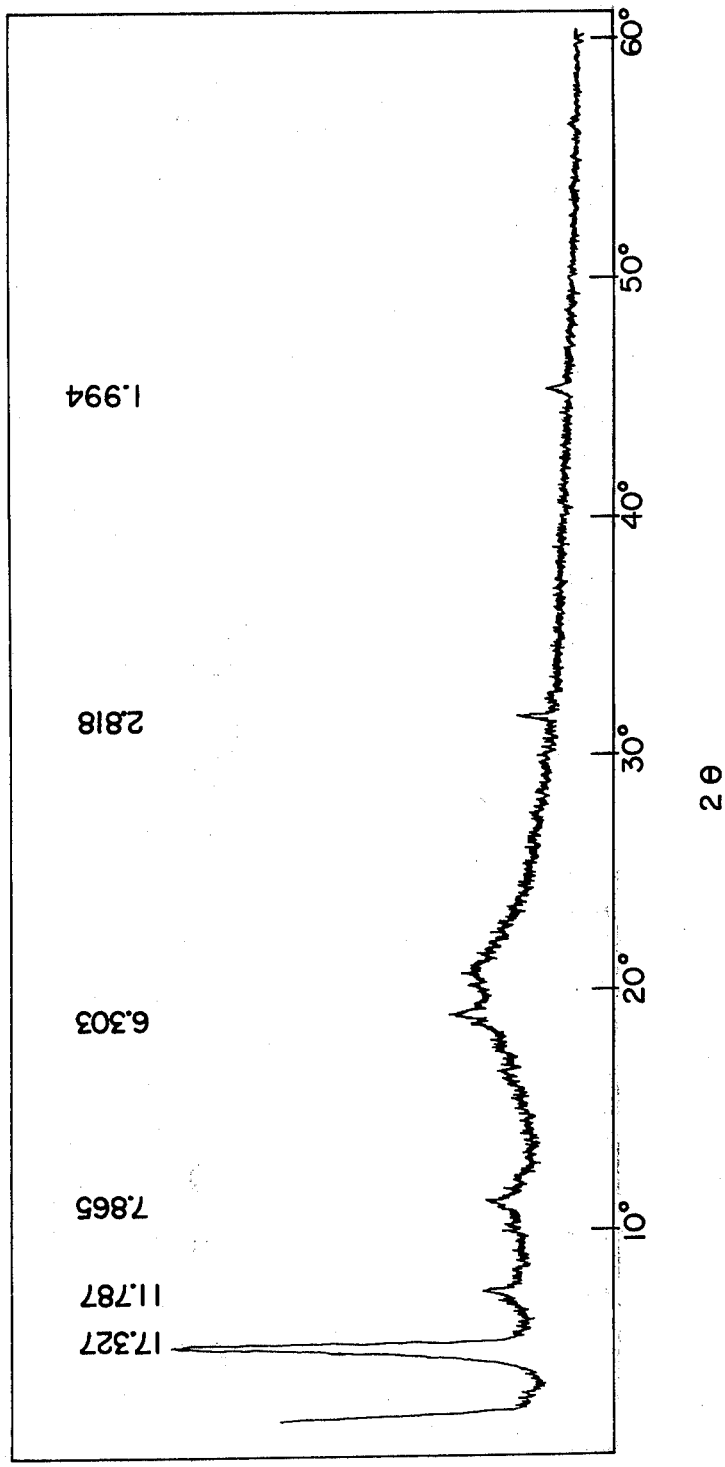
FIG. 2 is an X-ray diffraction pattern of the $DB_c$-AMP-$N_a$ crystallized from its solution in dioxane.
Figure 3:
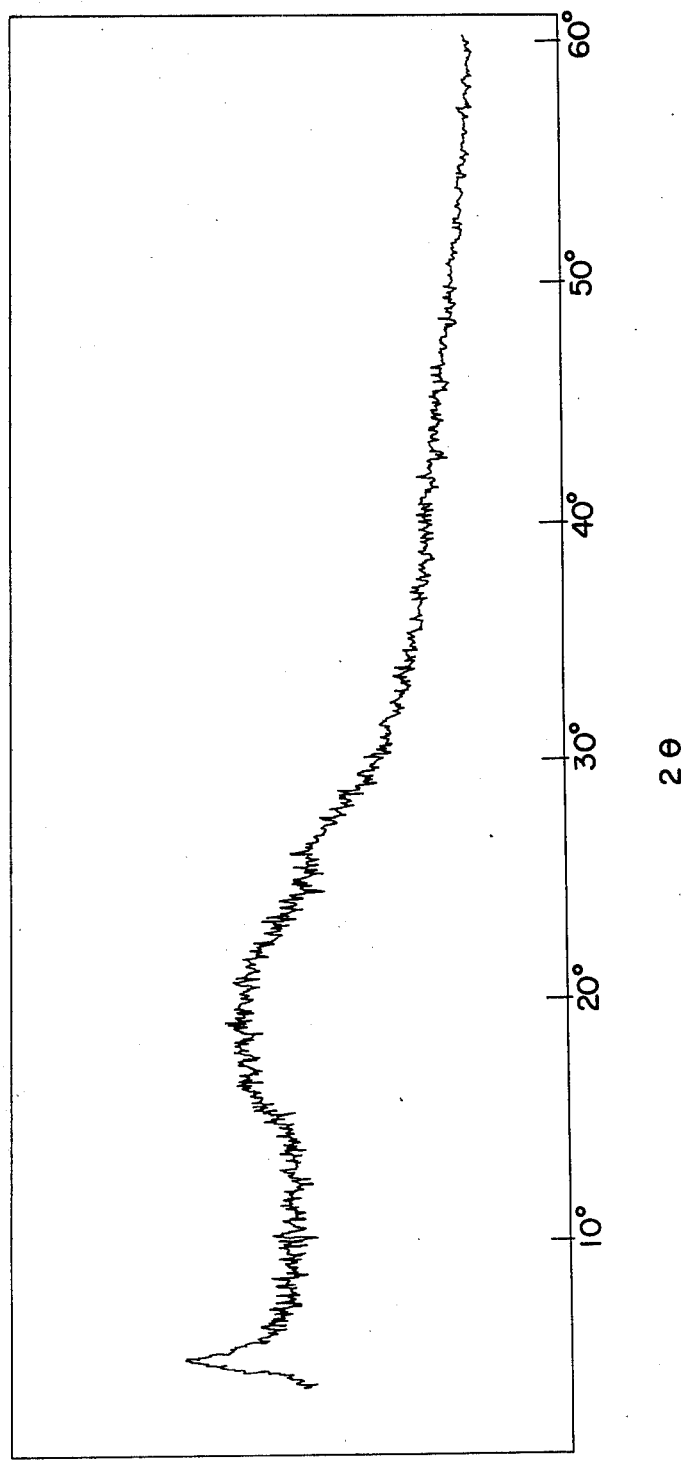
FIG. 3 is another X-ray diffraction pattern of a conventional amorphous $DB_c$-AMP-$N_a$ specimen.

The $DB_c$-AMP-$N_a$ according to this invention is of crystalline structure generally having a rectangular planar or needle shape crystal form which is white or transparent. The melting temperature of the crystalline $DB_c$-AMP-$N_a$ is 207° C to 209° C. Frequently, these crystals are in the form of twins or in a simply stuck state. As will be made apparent from the X-ray diffraction patterns shown in FIGS. 2 and 3, the crystalline $DB_c$-AMP-$N_a$ according to the present invention is crystallographically different from the conventional amorphous specimen.

More specifically, the crystalline $N^6,2'$-O-dibutyryl-adenosine-3',5'-cyclic monophosphate monosodium salt has the following X-ray diffraction lattice distance:

| Angstrom | Note |
|---|---|
| 1.994 | weak |
| 2.818 | weak |
| 6.303 | slightly weak |
| 7.865 | weak |
| 11.787 | weak |
| 17.327 | very intense |

The crystalline $DB_c$-AMP-$N_a$ according to the present invention is far superior to the conventional substance of the same kind because of its high purity, high stability, and low hydgroscopicity. Furthermore, the crystalline salt of this invention can be easily dried by subjecting it to ventilated air or by a vacuum drying process. The moisture content of the specimen thus dried can be made less than 6% by weight, or preferably 5 to 4% by weight. The results of the comparison between the conventional amorphous powdery specimen obtained through the freeze-drying process and the crystalline specimen according to the present invention are indicated in Table 1 below. Within in Table, the specimen A according to this invention is crystallized from an aqueous solution of $DB_c$-AMP-$N_a$ by the use of dioxane, and the specimen B is crystallized from an aqueous solution of $DB_c\text{-AMP-}N_a$ by the use of acetone.

Table 1

| Specimen | Days stored | Rate of decomposition (%) at 40° C | | | |
|---|---|---|---|---|---|
| | | 0 | 3 | 7 | 30 | 60 |
| Specimen prepared by conventional process (moisture content 5.87%) | | 1.46 | 3.60 | 4.91 | 10.81 | 14.08 |
| Specimen A (moisture content 4–14%) | | 0 | 0 | 0 | 0 | 0 |
| Specimen B (moisture content 3.98%) | | 0 | 0 | 0 | 0 | 0 |

The decomposition rate is indicated in % by weight of $N^6$-monobutyryl-adenosine-3′,5′-cyclic phosphate obtained as a result of the decomposition of the $DB_c\text{-AMP-}N_a$. As will be apparent from Table 1, the crystalline specimen of this invention is far more stable than the conventional powdery specimen.

Crystallization

Starting solution:

The crystalline $DB_c\text{-AMP-}N_a$ according to the present invention is produced from its starting solution through a specific crystallizing method, through which the solubility of the $DB_c\text{-AMP-}N_a$ in the solution is lowered by the addition of a non-solvent for it. According to the present invention, a limitation is imposed on the variety of the combination between the solvent for providing a starting solution of the $DB_c\text{-AMP-}N_a$ and the non-solvent to be added to the solution, and it is believed that such restriction is critical for the production of the crystalline $DB_c\text{-AMP-}N_a$.

The starting solution may be produced by dissolving amorphous $DB_c\text{-AMP-}N_a$ in water, aqueous alcohol, or in an alcohol, or it may otherwise be a product obtained through ordinary processes from adenosine-3′,5′-cyclic phosphoric acid. An example of the synthesis of the $DB_c\text{-AMP-}N_a$ is as follows.

7.5 g of adenosine-3′,5′-cyclic phosphoric acid is dissolved in a minimum quantity of 0.4 M aqueous triethyl amine. The solution is concentrated under reduced pressure to dryness, and is further subjected to azeotropic dehydration with about 50 ml. of pyridine under reduced pressure. To the triethylamine salt of adenosine-3′,5′-cyclic phosphoric acid thus dehydrated, 120 ml. of anhydrous pyridine is added and the resulting mixture is heated to dissolve at least a portion of the triethylamine salt. The mixture or solution is then cooled to about 30° C, and 100 ml. of anhydrous butyric acid [$(CH_3CH_2CH_2CO)_2O$] was added to the mixture and the mixture is caused to undergo reaction completely with stirring at a room temperature. The mixture is then ice-cooled, and 20 ml. of water is added to the cooled mixture to hydrolyze the unreacted excess anhydrous butyric acid. The product contains 10g of $DB_c\text{-AMP}$. The product is then neutralized with a sodium-based alkali to produce $DB_c\text{-AMP-}N_a$.

The aqueous solution of $DB_c\text{-AMP-}N_a$ thus obtained may be used directly, or, after it has been subjected to pretreatment and refining processes utilizing, for instance, ion-exchanging resin, it may be used as a starting solution for the crystallizing step of the present invention.

As described hereinbefore, the starting solution is an aqueous solution, aqueous alcoholic solution, or an alcoholic solution of $DB_c\text{-AMP-}N_a$. The alcohols to be used for the solvent should be hydrophilic alcohols which are soluble in water or those wherein water can be dissolved. Typical examples of such alcohols are those containing from 1 to 8, carbon atoms, particularly monohydroxy alcohols, dihydroxy alcohols, and trihydroxy alcohols containing from 1 to 4 carbon atoms, and more preferably monohydroxy alcohols containing from 1 to 4 carbon atoms. In other words, methanol, ethanol, n-propanol, iso-propanol, n-butanol, iso-butanol, n-pentanol, iso-pentanol, hexanol, heptanol, diethylene glycol mono $C_1 - C_4$ alkylether, etc. can be used as the solvent for the $DB_c\text{-AMP-}N_a$ in accordance with this invention.

Ordinarily, the solubility in an alcohol of the $DB_c\text{-AND }N_a$ in crystalline form is decreased with increase in the number of carbon atoms contained in the alcohol. For instance, the solubility of $DB_c\text{-AMP-}N_a$ in octanol is substantially reduced.

The solubility of $DB_c\text{-AMP-}N_a$ in various alcohols is also varied by the existence of water in the alcohols. In particular cases, where the $DB_c\text{-AMP-}N_a$ is dissolved in a higher alcohol, it is advantageous to use a suitable aqueous alcohol system. In such a system, the mixing ratio of water and alcohol is selected in an appropriate range.

It should be noted that polyhydric alcohols such as ethylene glycol, diethylene glycol, glycrol, etc. ordinarily have high viscosity and high boiling points, thus hampering the separation of crystals and drying operation of the solvent, may yet be used as a solvent of this invention. Furthermore, the above described alcoholic solution aqueous alcoholic solution, and aqueous solution of the $DB_c\text{-AMP-}N_a$ containing impurities such as solvents, reagents, salts, and coloring matters caused by the preceding synthetic reaction may also be used as a starting solution of the present invention.

The $DB_c\text{-AMP-}N_a$ content in the starting solution may be in a range from 20 to 80% by weight, or preferably in a range of from 30 to 70% by weight.

Crystallizing Solvents:

These solvents are fundamentally organic non-solvents for the $DB_c\text{-AMP-}N_a$ which are at least partially miscible with the solvent of the starting solution, especially the alcohol used. For this reason, these solvents are selected, in accordance with one aspect of the present invention, from a specific group of organic solvents. The crystallizing solvents must satisfy these fundamental requirements, and are selected from the group consisting of ethers, ketones, and esters. When the separation thereof from the crystals and dripability are considered, solvents of low boiling point are preferable.

Examples of the crystallizing solvents which can be used in practice are as follows.

Ethers: ethyl ether, dioxane, and tetrahydrofuran; Ketones: acetone, methyl ethyl ketone, and methyl isobutyl ketone; Esters: lower alkyl, preferably $C_1$ to $C_4$ alkyl, acetates such as methyl acetate, ethyl acetate, and propyl acetate (n- or -iso-). One of the above described solvents or two or more thereof mixed together with a suitable ratio may be used as the crystallizing solvent of this invention.

In the case where aqueous solution or aqueous alcoholic solution of $DB_c\text{-AMP-}N_a$ is used as a starting solution of this invention, the crystallizing solvent is selected with consideration of its hydrophilic nature, which should be promoted with increase in the mixing ratio of water. For instance, for the aqueous solution of aqueous alcoholic solution, containing a greater part of water (water content is more than 70% by weight), of $DB_c$-AMP-$N_a$, hydrophilic dioxane or acetone can be used advantageously. When a sufficient amount of the above-mentioned dioxane or acetone is used with their other crystallizing solvents, the latter component can be a hydrophobic solvent in which the solubility of $DB_c$-AMP-$N_a$ is low, and which is selected from ethers (other than dioxane), ketones (other than acetone), and esters.

In the case of the mixed use, no remarkable increase in the yield can be observed in comparison with the case where dioxane or acetone is used as described above independently or as a mixture. However, the above described use is advantageous for separation of the crystals from the solvent or for drying the crystals when the non-hydrophilic solvent thus selected has a low boiling point. The term "non-hydrophilic solvent" herein used is designated to mean solvents which are selected from the group of ethers, esters and ketones and which have a solubility in water of at most 25%.

Since more crystallizing solvent is required when the amount of water contained in the $DB_c$-AMP-$N_a$ solution increases, alcoholic solutions requiring minimum water contents, and thus alcohols which do not require water such as methanol, ethanol, and the like, are preferable as the solvent. This is apparent from the following Tables 2 and 3 showing the relation between the aqueous alcoholic solution containing 3g of $DB_c$-AMP-$N_a$ in a concentration of 20% by weight and the amount of dioxane as the crystallizing solvent.

Table 2

| Composition % by weight of solution to be crystallized | | | Amount of dioxane used (ml) | Yield of crystals (%) |
|---|---|---|---|---|
| $DB_c$-AMP-$N_a$ | ethanol | water | | |
| 20 | 0 | 80 | 600 | 94.1 |
| 20 | 20 | 60 | 350 | 94.5 |
| 20 | 40 | 40 | 300 | 95.7 |
| 20 | 60 | 20 | 200 | 96.8 |
| 20 | 70 | 10 | 150 | 97.3 |

Table 3

| Composition % by weight of solution to be crystallized | | | Amount of dioxane used (ml) | Yield of crystals (%) |
|---|---|---|---|---|
| $DB_c$-AMP-$N_a$ | methanol | water | | |
| 20 | 0 | 80 | 600 | 94.1 |
| 20 | 20 | 60 | 350 | 92.1 |
| 20 | 40 | 40 | 300 | 94.4 |
| 20 | 60 | 20 | 200 | 96.0 |
| 20 | 70 | 10 | 150 | 96.4 |

When water is used solely as the Solvent of $DB_c$-AMP-$N_a$, the required amount of the crystallizing solvent such as dioxane or acetone is varied in a wide range depending on the concentration of the $DB_c$-AMP-$N_a$ solution, and therefore it is desirable that the process of this invention to be carried out at a comparatively high concentration of the solution. From the commercial point of view, the concentration is selected in a range of 30 to 70%. That is, with a concentration thereof lower than 30%, the required amount of the dioxane or acetone is excessive although the crystals of $DB_c$-AMP-$N_a$ can be crystallized from the solution. On the other hand, with a concentration of more than 70%, or particularly more than 85%, the crystallization of $DB_c$-AMP-$N_a$ becomes difficult.

Relations between the added amounts of dioxane and acetone and the yields of the crystals when 6 g of $DB_c$-AMP-$N_a$ is dissolved in water with various concentrations, are indicated in Tables 4 and 5. From these Tables, the variation of the added amounts of dioxane and acetone for obtaining the above-mentioned yields of the crystals is apparent.

Table 4

| Composition % by weight of solution to be crystallized | | Dioxane | | |
|---|---|---|---|---|
| Concentration (% by weight) | Weight of solution | Added quantity (ml) | Added quantity per one g. of $DB_c$-AMP-$N_a$ (ml) | Yield (%) |
| 20 | 30.0 | 1200 | 200 | 94.1 |
| 30 | 20.0 | 500 | 83 | 94.9 |
| 50 | 12.0 | 200 | 33 | 97.2 |
| 70 | 8.5 | 100 | 17 | 97.0 |

Table 5

| Composition % by weight of solution to be crystallized | | Dioxane | | |
|---|---|---|---|---|
| Concentration (% by weight) | Weight of solution | Added quantity (ml) | Added quantity per one g. of $DB_c$-AMP-$N_a$ (ml) | Yield (%) |
| 20 | 30.0 | 1200 | 200 | 94.6 |
| 30 | 20.0 | 500 | 83 | 95.2 |
| 50 | 12.0 | 200 | 33 | 96.5 |
| 70 | 8.5 | 100 | 17 | 96.1 |

The crystallizing temperature is generally in a range of from 15° to 45° C, preferably from 20° to 40° C.

In the case were the crystallizing solvent consists of a plurality of solvents, the composition of the solvent or mixing ratio of the component solvents may be varied in accordance with time. For instance, a part of the solvents may be first added into the solution, and the rest of the solvents may thereafter be added after initiation of the crystallization thereby to improve the yield.

Direct Crystallization:

When the $DB_c$-AMP-$N_a$ in a crude crystalline state or in an amorphous state is brought into contact with a mixture of an alcohol of the above-mention nature and the crystallizing solvent also described above, the $DB_c$-AMP-$N_a$ once dissolved is crystallized as crystals such as for example rectangular planar crystals. The temperature at which the above-mentioned components are brought into contact is in a range of 15° to 45° C, or more preferably from 20° to 40° C. It is also possible to maintain the temperature in the initial part of the crystallizing period at a high level in a range of, for instance, from 40° to 45° C and to hold the temperature in the remaining period at a low level in a range of, for instance, from 15° to 20° C.

In this case, the mixing ratio of the two types of solvents is such that the weight ratio of an alcohol to the crystallizing solvent is within a range of, for instance, from 1:1 to 1:8, or preferably from 1:2 to 1:6.

The process according to the present invention will be better understood from the following examples thereof which are by no means of restrictive nature.

EXAMPLE 1

Water was added to a reaction product of triethylammonium adenoxine-3',5'-cyclic phosphate and anhydrous butyric acid produced as described hereinbefore and containing 10 g of $DB_c$-AMP (as well as some butyric acid and pyridine), and the resulting solution was neutralized with calcium hydroxide, and concentrated so that calcium butyrate was crystallized. The crystallized calcium butyrate was filtered off and was washed with ethanol. The filtrate together with the wash liquor was again neutralized to pH 7.0 with calcium hydroxide, and the thus produced crystallized calcium butyrate was again filtered out. The filtrate was then concentrated to remove organic solvent therefrom, added with water for obtaining an aqueous solution, and was treated with an ion-exchange resin thereby to remove calcium contents. The resultant solution was again neutralized by the addition of sodium hydroxide, concentrated to contain about 50% of $DB_c$-AMP-$N_a$, added with 350 ml of dioxane while the solution was agitated, and left as it was until $DB_c$-AMP-$N_a$ was crystallized. The crystals was then separated from the solvent, washed firstly by dioxane and then by ethylether, dried out at 50° C through ventilation, and further subjected to a vacuum-drying process over silica gel in a desiccator, so that 8.5 g of $DB_c$-AMP-$N_a$ in a crystalline state was obtained. This product had a moisture content of 2.8% and a purity of 98.6%.

EXAMPLE 2

500 ml of dioxane was added to 20 g of an aqueous solution containing 33% of $DB_c$-AMP-$N_a$, and the mixture was agitated and left standing thereby to crystallize $DB_c$-AMP-$N_a$. The crystals of $DB_c$-AMP-$N_a$ thus obtained were then filtered of and dried over silica gel in a vacuum desiccator, so that 6.4 g of $DB_c$-AMP-$N_a$ was obtained. The moisture content of this product was 3.06% and the purity thereof was 99.6%.

EXAMPLE 3

350 ml of dioxane was added to 20 g of an aqueous solution containing 55% of $DG_c$-AMP-$N_a$, and the mixture was agitated and left for an appropriate period. The crystals of $DB_c$-AMP-$N_a$ thus obtained were then filtered, washed with ethyl ether, and dried at 40° C through ventilation, so that 10.4 g of $DB_c$-AMP-$N_a$ crystals were obtained. The crystalline $DB_c$-AMP-$N_a$ had a moisture content of 3.81% and a purity of 99.3%.

EXAMPLE 4

400 ml of acetone was added to 20 g of an aqueous solution containing 50% of $DB_c$-AMP-$N_a$, and the mixture was agitated and left for an appropriate period of crystallizing $DB_c$-AMP-$N_a$. The crystals thereof were filtered, washed with ethyl-ether, and was dried through ventilation at 40° C and also in a vacuum desiccator over silica gel, so that 9.3 g of crystalline $DB_c$-AMP-$N_a$ was obtained. The product has a moisture content of 2.95% and a purity of 99.6%.

EXAMPLE 5

300 ml of dioxane and 100 ml of acetone were added to 20 g of a 50% aqueous solution of $DB_c$-AMP-$N_a$, the mixture was then agitated, left standing for crystallization, and the crystalline $DB_c$-AMP-$N_a$ thus obtained was filtered, washed with ethyl-ether, dried under the ventilation of air at 40° C, and further dried over phosphorus pentoxide in a vacuum desiccator, whereby 9.6 g of $DB_c$-AMP-$N_a$ crystals were obtained. The moisture content in the crystals was 1.80% and the purity thereof was 99.7%.

EXAMPLE 6

280 ml of dioxane was added to 20 g of a 55% aqueous solution of $DB_c$-AMP-$N_a$, 80 ml of ethyl-ether was added little by little while the solution was agitated. The crystals of $DB_c$-AMP-$N_a$ thus obtained were separated from the solution, washed with ethyl-ether, dried through ventilated air at 40° C, and further dried over silica gel in a vacuum desiccator, whereby 10.8 g of crystalline $DB_c$-AMP-$N_a$ was obtained. The moisture content of the product was 3.51% and the purity thereof was 99.7%.

EXAMPLE 7

300 ml of acetone was added to 20 g of a 55 % aqueous solution of $DB_c$-AMP-$N_a$, agitated for a period, and 70 ml of ethyl acetate was added little by little to the above described solution. The mixture was then agitated and left standing for crystallization. The crystalline $DB_c$-AMP-$N_a$ thus obtained was separated from the solution, and dried over silica gel in vacuum disiccator, whereby 10.8 g of crystalline $DB_c$-AMP-$N_a$ was obtained. The moisture content of the crystals was 3.66% and the purity thereof was 98.9%.

EXAMPLE 8

350 ml of dioxane was added to 20 g of a 50% solution of $DB_c$-AMP-$N_a$. The mixture was agitated, and then 50 ml of methyl ethyl ketone was added then the $DB_c$-AMP-$N_a$ started to crystallize. The mixture was agitated and left standing for crystallization. The crystalline $DB_c$-AMP-$N_a$ thus obtained was separated from the solvent, washed with ethyl-ether, and dried over silica gel in a desiccator. The moisture content of the resultant crystalline $DB_c$-AMP-$N_a$ was 3.38% and the purity thereof was 99.1%.

EXAMPLE 9

A reaction product of triethylammonium adenosine-3',5'-cyclic phosphate and anhydrous butyric acid produced as described hereinbefore and containing 10 g of $DB_c$-AMP (further containing butyric acid and pyridine) was added with water, neutralized with calcium hydroxide, and concentrated. The calcium butyrate crystallized was then filtered off and washed with ethanol. The filtrate was again neutralized to pH 7.0 with calcium hydroxide thereby to further remove calcium butyrate, and also concentrated for removing pyridine. The filtrate was further added with water and treated with an ionexchange resin thereby to remove calcium contents. The filtrate was then neutralized with sodium hydroxide, concentrated to about 10% concentration, and the pH thereof was adjusted to 7.0 with sodium hydroxide. The solution was then agitated, and sodium chloride was added until the solution was saturated therewith and the crystalline $DB_c$-AMP-$N_a$ was thereby salted out, 100 ml of a mixed solvent consisting of dioxane and methanol at 1:1 was added to the precipitate, whereby $DB_c$-AMP-$N_a$ was dissolved into the mixed solvent. The non-soluble materials were then filted off, and the filtrate was concentrated and dried into solid state. Such a desalting process was repeated four times, and the solid substance thus obtained was then dissolved in 25 ml of mixed solvent consisting of ethanol and dioxane mixed at a ratio of 1:2. 100 ml of dioxane was thereafter added to the solution after crystallization thereof started thereby to complete the crystallization. The crystals were then separated from the solvent, washed with ethyl-ether, and dried by ventilated air at 60 °C. The crystals were further dried over silica gel in a vacuum desiccator, and 8.6 g of crystalline $DB_c$-AMP-$N_a$ was obtained. The moisture content thereof was 2.5%, and the purity thereof was 99.4%.

A comparison test was carried out as to the stability between the crystalline $DB_c$-AMP-$N_a$ and the conventional amorphous powdery sample (moisture content 5.87%) of $DB_c$-AMP-$N_a$, and it was found that the crystalline sample of this example was absolutely stable having no recognizable decomposition while the conventional sample showed decomposition of 10.81% and 14.08% after 30 days and 60 days of storage, respectively, at 40° C.

EXAMPLE 10

21 ml of ethanol was added to 9 g of a 67% solution of $DB_c$-AMP-$N_a$. 150 ml of dioxane was further added to the mixture while it was agitated. The resultant crystalline matter was separated from the solution and dried thereby to produce 6.0 g of crystalline $DB_c$-AMP-$N_a$. The moisture content of the product was 3.6% and the purity thereof was 99.8%. The crystalline $DB_c$-AMP-$N_a$ did not show any decomposition after 60 days' storage at 40° C.

EXAMPLE 11

20 ml of methanol was added to 9 g of a 67% aqueous solution of $DB_c$-AMP-$N_a$. The mixture was further added with 150 ml of acetone while the former was agitated. The resultant crystalline matter was separated from the solution, and then dried to obtain 5.9 g of crystalline $DB_c$-AMP-$N_a$. The moisture content of this product was 3.5% and the purity thereof was 99.5%. After 60 days' storage test at 40° C, it was found that the crystalline $DB_c$-AMP-$N_a$ was absolutely stable.

EXAMPLE 12

10 ml of ethanol and 10 ml of dioxane were added to 6.4 g of amorphous powdery $DB_c$-AMP-$N_a$ of moisture content of 5.8%, and the mixture was crystallized after agitation. The crystallization was made complete by further addition of 90 ml of dioxane. The crystalline matter was then separated from the solvent, and dried to obtain 5.9 g of crystalline $DB_c$-AMP-$N_a$ having a moisture content of 2.8% and a purity of 99.5%. The product was found to be stable after the storage test for 60 days at 40° C.

EXAMPLE 13

10 ml of methanol and 20 ml of ethyl ether were added to 5 g of a product containing 80% of $DB_c$-AMP-$N_a$. The mixture was agitated and further added with 50 ml of ethyl ether then crystallization started. The mixture was further agitated, and the crystalline matter was separated from the mixed solution. The crystalline product was then dried to obtain 3.9 g of the crystalline $DB_c$-AMP-$N_a$. The crystalline product had a moisture content of 3.0% and a purity of 99.8%. It was found that the crystalline product was absolutely stable after the storage test for 60 days at 40° C.

EXAMPLE 14

20 ml of methanol was added to 8 g of a product containing 75% of $DB_c$-AMP-$N_a$. The mixture was agitated while 150 ml of ethyl acetate was added, and the resulting crystalline product was separated from the solution and dried to thereby produce 6 g of crystalline $DB_c$-AMP-$N_a$. The moisture content thereof was 4.1%, and the purity thereof was 99.1%. The crystalline $DB_c$-AMP-$N_a$ was found to be stable during 60 days' storage test at 40° C.

EXAMPLE 15

A mixed solvent comprising 10 ml of ethanol and 10 ml of methyl ethyl ketone was added to 6.4 g of amorphous powdery $DB_c$-AMP-$N_a$ of a moisture content of 5.8%, and agitated for crystallization. 80 ml of methyl ethyl kenone was further admixed to the solution to make the crystallization thereof complete, and the crystalline product was then separated from the solution. The crystalline product thus separated was then dried to obtain 5.9 g of crystalline $DB_c$-AMP-$N_a$. It was found that the product contains 3.1% of moisture and the purity thereof was 98.9%. After 60 days' storage test at 40° C, the product did not exhibit any decomposition.

EXAMPLE 16

A mixed solvent comprising 10 ml of ethanol and 10 ml of ethyl acetate was added to 5 g of a product containing 80% of $DB_c$-AMP-$N_a$, the mixture was agitated and further added with 70 ml of methyl acetate at the time of the crystallization started out of the mixture. Agitation was further continued until the substantial part of $DB_c$-AMP-$N_a$ was crystallized, and the resultant crystals were separated from the solution and dried to obtain 3.8 g of crystalline $DB_c$-AMP-$N_a$. The moisture content of this product was 3.3%, and the purity thereof was 99.3%. The product was found to be absolutely stable during 60 days' storage test at 40° C.

EXAMPLE 17

20 ml of n-propanol and 2 ml of water were added to 6.1 g of amorphous powdery $DB_c$-AMP-$N_a$ of a moisture content of 1.5% thereby to dissolve it in the mixed solvent. The solution was agitated while 200 ml of dioxane was added, and the crystallized product was separated from the solvent and dried to obtain 6.1 g of crystalline $DB_c$-AMP-$N_a$. The resultant product contained 3.6% of moisture and the purity thereof was 98.8%. It was found that the thus produced crystalline $DB_c$-AMP-$N_a$ was absolutely stable during 60 days' storage test at 40° C.

EXAMPLE 18

20 ml of n-butanol and 2 ml of water were added to 6.1 g of amorphous $DB_c$-AMP-$N_a$ of a moisture content of 1.5%. The solution was agitated while 200 ml of acetone was added thereto and the crystalline product produced was separated from the solution. The crystalline product was then dried to obtain 6.0 g of crystalline $DB_c$-AMP-$N_a$. The product had a moisture content of 2.2% and a purity of 98.8% and was absolutely stable during the storage test for 60 days at 40° C.

What is claimed is:

1. Crystalline $N^6,2'$-O-dibutyryl-adenosine-$3',5'$-cyclic monophosphate, monosodium salt, produced by the step of causing a crystallizing solvent selected from a group consisting of ethyl ether, tetrahydrofuran, dioxane acetone, diethyl ketone, methyl ethyl ketone, or an ester selected from $C_1$-$C_4$ alkyl acetates to contact an alcoholic solution, an aqueous alcoholic solution, wherein the alcohol is selected from the group consisting of methanol, ethanol, propanols, and butanols, or a simple aqueous solution of the $N^6,2'$-O-dibutyryladenosine-3',5'-cyclic monophosphate, monosodium salt, said crystallizing solvent being of such a nature that said N⁶,2'-O-dibutyryl-adenosine-3',5'-cyclic monophosphate monosodium salt is insoluble in it but it is at least partly miscible with the solvent constituting said solution, said crystalline salt having the following lattice distance upon X-ray diffraction:

| Angstrom | Note |
|---|---|
| 1.994 | weak |
| 2.818 | weak |
| 6.303 | slightly weak |
| 7.865 | weak |
| 11.787 | weak |
| 17.327 | very intense |

2. Crystalline N⁶,2'-O-dibutyryl-adenosine-3',5'-cyclic monophosphate monosodium salt as set forth in claim 1, wherein the moisture content thereof is less than 6% by weight.

3. Crystalline N⁶,2'-O-dibutyryl-adenosine-3',5'-cyclic monophosphate monosodium salt as set forth in claim 1, wherein the moisture content thereof is less than 4% by weight.

4. A process for producing crystalline N⁶,2'-O-dibutyryl-adenosine-3',5'-cyclic monophosphate monosodium salt comprising the step of causing a crystallizing solvent selected from a group consisting of ethyl ether, tetrahydrofuran, dioxane acetone, diethyl ketone, methyl ethyl ketone, or an ester selected from $C_1$ to $C_4$ alkyl acetates to contact an alcoholic solution, an aqueous alcoholic solution, wherein the alcohol is selected from the group consisting of methanol, ethanol, propanols, and butanols, or a simple aqueous solution of the N⁶,2'-O-dibutyryl-adenosine-3',5'-cyclic monophosphate monosodium salt, said crystallizing solvent being of such a nature that said N⁶,2'-O-dibutyryl-adenosine-3',5'-cyclic monophosphate monosodium salt is insoluble in it but it is at least partly miscible with the solvent constituting said solution.

5. A process for producing crystalline N⁶,2'-O-dibutyryl-adenosine-3',5'-cyclic monophosphate monosodium salt wherein at least one crystallizing solvent selected from the group consisting of dioxane and acetone is brought into contact with an aqueous solution of the N⁶,2'-O-dibutyryl-adenosine-3',5'-cyclic monophosphate monosodium salt, thereby to crystallize the same out of the solution.

6. A process for producing crystalline N⁶,2'-O-dibutyryl-adenosine-3',5'-cyclic monophosphate monosodium salt wherein a mixture of (1) at least one crystallizing solvent selected from the group consisting of dioxane and acetone and (2) a hydrophobic organic solvent soluble in said crystallizing solvent and selected from the group consisting of ethyl ether, tetrahydrofuran, methyl ethyl ketone, diethyl ketone, or an ester selected from $C_1$ to $C_4$ alkyl acetates is brought into contact with an aqueous solution of the N⁶,2'-O-dibutyryl-adenosine-3',5'-cyclic monophosphate monosodium salt to crystallize the same out of the solution.

7. A process for producing crystalline N⁶,2'-O-dibutyryl-adenosine-3',5'-cyclic monophosphate monosodium salt comprising the step of causing a crystallizing solvent selected from the group consisting of ethyl ether, tetrahydrofuran, dioxane, acetone, diethyl ketone, methyl ethyl ketone or an ester selected from $C_1$ to $C_4$ alkyl acetates to contact an alcoholic solution or aqueous alcoholic solution, wherein the alcohol is selected from the group consisting of methanol, ethanol, propanols and butanols, of the N⁶,2'-O-dibutyryl-adenosine-3',5'-cyclic monophosphate monosodium salt, said crystallizing solvent being of such a nature that said N⁶,2'-O-dibutyryl-adenosine-3',5'-cyclic monophosphate monosodium salt is insoluble in it but it is at least partly miscible with the solvents constituting said solution.

8. A process as set forth in claim 7, wherein said crystallization is carried out at a temperature ranging from 15° to 45° C.

9. A process for producing crystalline N⁶,2'-O-dibutyryl-adenosine-3',5'-cyclic monophosphate monosodium salt comprising the step of causing the N⁶,2'-O-dibutyryl-adenosine-3',5'-cyclic monophosphate monosodium salt in a solid state to contact a mixture consisting essentially of an alcohol in which said salt is soluble and which is selected from the group consisting of methanol, ethanol, propanols and butanols, and a crystallizing solvent which is miscible with said alcohol but in which said N⁶,2'-O-dibutyryl-adenosine-3',5'-cyclic monophosphate monosodium salt is insoluble and which is selected from the group consisting of ethyl ether, tetrahydrofuran, dioxane, acetone, diethyl ketone, methyl ethyl ketone, or an ester selected from $C_1$ to $C_4$ alkyl acetates, while said mixture is agitated, thereby to obtain the N⁶,2'-O-dibutyryl-adenosine-3',5'-cyclic monophosphate monosodium salt in a crystal form.

* * * * *